United States Patent [19]

Biskup et al.

[11] Patent Number: 5,449,818
[45] Date of Patent: Sep. 12, 1995

[54] PROCESS FOR THE PREPARATION OF AROMATIC DIISOCYANATES

[75] Inventors: Klaus Biskup, Bayerwerk; Christian König, Kaarst; Eckart Waldau, Düsseldorf, all of Germany

[73] Assignee: Bayer Aktiengesellschaft, Leverkusen, Germany

[21] Appl. No.: 61,977

[22] Filed: May 17, 1993

[30] Foreign Application Priority Data

May 22, 1992 [DE] Germany ............... 42 17 019.2

[51] Int. Cl.$^6$ ............................................. G07C 263/10
[52] U.S. Cl. ............................................. 560/347
[58] Field of Search ................................ 560/347

[56] References Cited

U.S. PATENT DOCUMENTS 4,419,295  12/1983  Hennig et al. ............... 260/453
4,847,408  7/1989  Frosch et al. ............... 560/347

OTHER PUBLICATIONS

Chem.-Ing.-Techn. 44 (1972), p. 1051 ff.
Appl. Sci. Res. (The Hauge) A3 (1953) p. 279 ff.

*Primary Examiner*—José G. Dees
*Assistant Examiner*—Samuel Barts
*Attorney, Agent, or Firm*—Joseph C. Gil; Lyndanne M. Whalen

[57] ABSTRACT

A continuous process for the preparation of aromatic diisocyanates by phosgenation of the corresponding diamines, in which the reaction is carried out in the gas phase. The mean contact time for the gaseous reactants is from 0.5 to 5 seconds with a mean deviation of no more than 6%. The product diisocyanate is obtained in yields of over 95%.

9 Claims, No Drawings

PROCESS FOR THE PREPARATION OF AROMATIC DIISOCYANATES

BACKGROUND OF THE INVENTION

The present invention relates to a continuous process for the preparation of aromatic diisocyanates by phosgenation of the corresponding diamines which is carried out in the gas phase.

Although the preparation of organic isocyanates from the corresponding amines by reaction with phosgene in the gas phase has long been known (e.g., Siefken, Ann. 562, 108 (1949)), the process has, until now, only been of technical importance for monoamines (e.g., Ullmann, 4th Ed. Vol. 13, p. 353) and (cyclo)aliphatic diamines. For instance, (cyclo)aliphatic diisocyanates can be successfully prepared in the gas phase in accordance with EP-A 289 840 at temperatures of 300° to 500° C. in a reaction tube with reaction times of $10^{-4}$s. Aromatic diamines, on the other hand, have been phosgenated in the liquid phase (e.g., Ullmann, 4th Ed. Vol. 13, p. 351) to produce the corresponding diisocyanates. Gas-phase reaction of aromatic diamines with phosgene has failed due to the formation of solids which blocked up the equipment and reduced the yield of diisocyanate.

The formation of solids can be ascribed to both excessively long and excessively short reaction-times. With short reaction times, isocyanate amino hydrochlorides are formed in addition to polyurea dust. With excessively long reaction times, carbodiimides and isocyanurates are formed.

SUMMARY OF THE INVENTION

It is an object of the present invention to provide a process for the preparation of diisocyanates in high yield in which phosgene and an amine are reacted in the gas phase. This and other objects which will be apparent to those skilled in the art are accomplished by limiting the mean contact time of the phosgene and diamine vapors to 0.5 to 5 seconds ±6%.

DETAILED DESCRIPTION OF THE PRESENT INVENTION

It has now been discovered that it is possible to prepare aromatic diisocyanates while avoiding solid substances which block up the reactors, and to achieve yields of over 95% (generally 99% and above) as a result of gas-phase reaction if the contact between phosgene and aromatic diamine is kept within a very narrowly restricted contact time spectrum (residence time spectrum in the reactor).

The necessary residence time for the reaction of both amine groups with the phosgene to form isocyanate is between 0.5 and 5 seconds, depending on the reaction temperature, the molar ratio of amine and phosgene used, dilution of the gaseous reaction partners with inert gases and the type of diamine used.

If the minimal residence time for the complete reaction, once this has been determined for the system in question (determined on the basis of temperature, molar ratio, dilution gas, diamine), is exceeded by less than about 20%, preferably less than 10%, the formation of additional reaction products such as isocyanurates and carbodiimides can effectively be avoided.

Within this contact time spectrum, which for chemical reactions is very narrow, the reactants must be mixed as homogeneously as possible and the remaining reaction time must be provided without back mixing. Back mixing causes a widening of the contact time spectrum.

The present invention is a process for preparing aromatic diisocyanates by reaction of corresponding diamines with phosgene in the gas phase. In this process, phosgene and diamine are reacted at a temperature above the boiling-point of the diamine and within a mean contact time of 0.5 to 5 seconds, preferably 1.0 to 3.7 seconds. The mean deviation from the mean contact time should amount to less than 6%, preferably less than 4%.

The process of the present invention is carried out in a manner such that the reactants are introduced into suitable reactors at a temperature above the boiling temperature of the diamine, mixed and reacted. The isocyanate is then condensed by cooling the gas flow to a temperature above the decomposition temperature of the corresponding carbamic chloride.

For the practical implementation of the process of the present invention, the deviation from the mean contact time is essentially determined by the time necessary to bring about mixing of the reaction partners. As long as the reaction partners are not mixed homogeneously, the reactor still contains unmixed gas volumes which have as yet not managed to come into contact with the reaction partner.

Mixing of the reactants should therefore be achieved within 0.1 to 0.3 seconds until a degree of segregation of $10^{-3}$ has been achieved. The degree of segregation is a measure of the incompleteness of the mixing process (see, e.g., Chem.-Ing.-Techn. 44 (1972), p. 1051 ff; Appl. Sci. Res. (The Hague) A3 (1953), p. 279).

Methods for implementing short mixing times are well known in principle. Suitable techniques include mixing aggregates with agitated or static mixing devices. Static mixing devices are preferred. The dependence of the degree of segregation on the relative length of the mixing tube (ratio of the length of the mixing path to the diameter) for some static mixing aggregates is shown in Chemie-Ing.-Techn. 44 (1972) pp. 1051–1056. From the length of the mixing path, the volumetric flow rate of the reactants can be calculated for a particular mixing aggregate. Knowledge of this flow rate is necessary in order to stay within the mixing time permissible in accordance with the present invention.

Jet mixers are particularly preferred devices in which to carry out the process of the present invention. For example, when a jet mixer is used to carry out the process of the present invention, one component (e.g., diamine) is blown at high speed into a mixing tube through a concentric tube of small diameter (nozzle) into the flow of the other component (phosgene). Mixing with a degree of segregation of $10^{-3}$ is achieved at a distance of four times the tube diameter from the discharge end of the nozzle (Chemie-Ing.-Techn. 44 (1972) p. 1055, Diag. 10). Concrete dimensions for such jet mixers can be calculated from the available experimental data on the basis of the laws of similarity for fluid mechanics.

In order to achieve as high a degree of segregation as possible for a short mixing path, the momentum ratio of the gas flows in the jet mixer is also important. For a given mixing aggregate, the momentum of the central gas jet (diamine) can be increased by diluting with a dilution gas that is inert with respect to the reaction.

Nitrogen is preferably used as the dilution gas. Vapors of chlorobenzene, o-dichlorobenzene, xylene, chloronaphthalene, decahydronaphthalene or the like, and mixtures thereof are also suitable. The volume ratio of diluent to diamine may typically be between 1:0.5 and 1:2.

After the reaction components have been mixed, the reaction mixture flows through the mixing tube which has been extended by the reaction chamber in order to provide the remaining reaction time. The flow through the reaction chamber should be in the form of a plug with a flow of up to about 90%, so that all parts by volume of the flow have approximately the same flow time (in order to restrict further widening of the distribution of contact time between the reactants as much as possible). An almost ideal plug flow can be produced as a result of highly turbulent flows with Reynolds numbers higher than 4000 in the empty tubular reactor. Due to the high flow rates consequently required, the necessary residence time can only be achieved in very long mixing tubes and reactor tubes.

The plug flow can also be generated at a lower flow rate by placing fitments in the reaction tube, said fitments having the effect of opposing the formation of a laminar flow profile and bringing about the formation of a level flow front. The fitments may, e.g., take the form of three-dimensional fine-mesh wire netting or packing material.

The degree of realization of the ideal plug flow (with a mean deviation from the mean residence time equal to 0) may be described in flow technology by means of the Bodenstein number BO (Determination of the BO number is described, e.g. in Fitzer, Techn. Chemie, Springer 1989, 288 to 295).

In accordance with the present invention, the Bodenstein number should be at least 100, preferably at least 250.

Another method to describe the degree of realization of the ideal plug flow (with a mean deviation from the mean residence time equal to 0) is by means of a dimensionless group which determines the intensity of axial dispersion. In some articles it is called the reactor dispersion group, e.g. Levenspiel and Bischoff in Drew et al. (Editors) Adv. in Chem. Eng. Vol.4, Acad. Press, NY 1963.

In accordance with the present invention, the reactor dispersion group should have values of at most 0.01, preferably at most 0.004.

The present invention is a process for preparing diisocyanates of the general formula

OCN—R—NCO in which
R represents a hydrocarbon residue with at least one aromatic system, by phosgenation of the corresponding diamines of the general formula

H$_2$N—R—NH$_2$ in the gas phase. In the preferred embodiments of this process,
a) the vaporous diamines, optionally diluted with an inert gas or with the vapors of an inert solvent, and phosgene are heated separately to temperatures of from 200° to 600° C. and mixed continuously in a static mixing device within a period of 0.1 to 0.3 seconds until a degree of separation of at least 10 is achieved;
b) the reaction mixture which leaves the mixing device (subject to the avoidance of back-mixing) is continuously conveyed through a tubular reaction chamber maintained at a temperature of 200° to 600° C. (where the reaction is completed), with a flow characterized either by a Reynolds number of more than 4000, or a Bodenstein number of more than 100, or a value for the reactor dispersion group of less than 0.01;
c) the gas mixture issuing from the reaction chamber is cooled to condense the diisocyanate formed with the temperature being maintained above the decomposition temperature of the carbamic chloride corresponding to the diisocyanate;
d) uncondensed diisocyanate is separated off from the gas mixture by washing with an inert solvent; and
e) the inert solvent is recovered by distillative processing.

The process of the present invention permits the reaction of undecomposed vaporizable aromatic diamines of the general formula

H$_2$N—R—NH$_2$ in which
R represents a hydrocarbon residue which contains at least one aromatic system and which may be substituted by additional residues, such as alkyl groups, halogen atoms, or ether groups.

The amine groups of the diamines may both be linked to one and the same aromatic system in the hydrocarbon residue R or they may be bonded to two different aromatic systems.

Typical examples of suitable diamines are the pure isomers and isomer mixtures of diaminobenzene, diaminotoluene, diaminodimethylbenzene, as well as diaminodiphenylmethane. Preferred starting materials are 2,4/2,6-toluenediamine mixtures with isomer ratios of 65/35 and 80/20 and the pure 2,4-isomer.

The phosgene employed in the phosgenation reaction is used in excess relative to the diamine. In general, a quantity of phosgene which corresponds to 150 to 250% of the theoretical stoichiometric amount for the phosgenation reaction taking place is sufficient.

Prior to carrying out the process of the present invention, the phosgene is heated to a temperature within the range of 200° to 600° C., preferably 300° to 400° C.

After the phosgenation reaction has taken place in the tubular reactor, the gaseous mixture issuing continuously from the tubular reactor is liberated from the diisocyanate formed. This can, for example, be achieved in one step by selective condensation in an inert solvent, as has already been recommended for other gas-phase phosgenations (EP 0 289 840). In this separation procedure, the temperature is chosen so that it is above the decomposition temperature of the carbamic chloride corresponding to the diisocyanate but below the condensation temperature of the diisocyanate and any solvent used concomitantly in the vapor flow as diluent. The diisocyanate condenses or dissolves in the solvent while excess phosgene, hydrogen chloride and, where appropriate, inert gas used concomitantly as diluent pass through the condensation step or the solvent in the gaseous state. Particularly suitable for selective recovery of the diisocyanate from the mixture leaving the tubular reactor in the gaseous state are solvents maintained at a temperature of from 80° to 200° C., preferably 80° to 180° C. Suitable solvents have been identified above. Particularly preferred solvents are technical dichlorobenzene and decahydronaphthalene.

Generation of the flow of the gaseous reaction mixture as plug flow without back-mixing is essential to the process of the present invention. Such flow of the mixture issuing from the mixing aggregate through the tubular reactor is ensured by a difference in pressure between the product feed pipes leading to the mixing aggregate and the outlet for the condensation step. In general, the pressure in the feed pipes leading to the mixing aggregate lies within the range of from 200 to 3000 mbar, and the pressure downstream of the condensation step lies within the range of from 150 to 2000 mbar. It is essential that a pressure differential be maintained for the purpose of ensuring the stated directional flow.

The gas mixture leaving the condensation step is then liberated from excess phosgene in known manner. This can be achieved by means of a cold trap, adsorption in an inert solvent maintained at a temperature of $-10°$ C. to 8° C. (e.g., chlorobenzene or dichlorobenzene), or by adsorption and hydrolysis on activated carbon. The hydrogen chloride gas passing through the phosgene-recovery step can be recycled in known manner with a view to recovering the chlorine required for phosgene synthesis.

Isolation of the diisocyanates is achieved by distillative processing of the solutions resulting from the condensation step.

Having thus described our invention, the following Examples are given as being illustrative thereof. All percentage figures given in these Examples are percentages by weight.

EXAMPLES

Example 1

Through a nozzle of 1 mm internal diameter, projecting for 20 mm into a tubular reactor 500 mm in length and with a diameter of 25 mm, continuously flowed a mixture of 0.5 mol/h of a gaseous isomer mixture of 2,4- and 2,6-toluenediamine (TDA; 80% 2,4-isomer and 20% 2,6-isomer) into a heat exchanger heated to 420° C. with 0.8 mol/h nitrogen.

Simultaneously, through the annular gap between nozzle and reactor wall, flowed 2.25 mol/h phosgene which was also preheated to 420° C. 50 mm behind the TDA nozzle was the beginning of fine-mesh packing material which filled the rest of the reactor. The tubular reactor was heated externally by means of a heating bath at a temperature of 310° C. The reaction mixture had a residence time in the tubular reactor of about 3 sec. The Reynolds number was about 210. The Bodenstein number was greater than 1000. The reactor dispersion group had a value of less than 0.001.

The hot reaction mixture leaving the reactor in the gaseous state was conveyed through an isocyanate absorption column in which the diisocyanate condensed as a result of vaporization of dichlorobenzene conveyed in the counterflow. The vaporized dichlorobenzene condensed totally in a reflux condenser placed downstream and served as reflux of the isocyanate absorption column when supercooled.

The gas mixture issuing from the reflux condenser, which included chlorinated hydrocarbon, phosgene and nitrogen, was liberated from phosgene and chlorinated hydrocarbon in a subsequent activated-carbon scrubbing tower sprayed with water.

By the application of a vacuum downstream of the activated carbon scrubbing tower, a pressure of 800 mbar was maintained at the end of the tubular reactor. The pressure at the product feed pipes leading to the mixing chamber amounted to 820 mbar for the mixture of toluenediamine vapor and nitrogen, and 815 mbar for the phosgene.

The toluene diisocyanate formed was removed in a mixture with dichlorobenzene from the sump of the isocyanate scrubbing column and then obtained in pure form by distillation. The yield of toluene diisocyanate was 99.3%. The tubular reactor showed no sign of being blocked.

Example 2

Using the stone equipment and process conditions of Example 1, 1.5 mol/h toluenediamine, not diluted with nitrogen, were reacted with 6.15 mol/h phosgene. The residence time in the tubular reactor amounted to 1.2 sec. The Reynolds number was about 500. The Bodenstein number was about 1000, corresponding to a reactor dispersion group value of approximately 0.001.

The yield of toluene diisocyanate was 99.1%.

Example 3

Using the same type of equipment and the same process conditions of Example 1, the residence time was reduced to less than 1 second by the use of a reactor which was only 120 mm in length.

The yield of toluene diisocyanate was 98.3%.

Example 4 (Comparative)

Under the process conditions of Example 1, 0.5 mol/h toluenediamine in a mixture with 0.8 mol/h nitrogen were caused to react with 3.5 mol/h phosgene. The tubular reactor contained no packing elements. The residence time amounted to about 2 sec. The Reynolds number was about 250. The Bodenstein number was about 20, corresponding to a reactor dispersion group value of about 0.05.

The experiment was halted after 10 minutes because solids blocked up the isocyanate scrubbing column.

Example 5

In the apparatus of Example 1, 0.5 mol/h 4,4'-diaminodiphenylmethane was heated to 410° C. in a mixture with 0.8 mol/h nitrogen and caused to react with 3.5 mol/h phosgene at 400° C. The residence time in the reactor, which was filled with packing elements, amounted to 2.3 sec. The reactor was kept at a temperature of 400° C. by means of a heating bath. The pressure at the end of the reaction tube amounted to 600 mbar. Condensation was carried out in dichlorobenzene.

The yield of diphenylmethane-4-4'-diisocyanate was 99.1%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an aromatic diisocyanate comprising reacting a diamine and phosgene at a temperature above the boiling point of the diamine within a mean contact time of from 0.5 to 5 seconds with a mean deviation in the contact time of no more than 6%.

2. The process of claim 1 in which the diamine and phosgene are heated separately to a temperature of from about 200° to about 600° C. and mixed continuously in a static mixing device within a period of from 0.1 to 0.3 seconds.

3. The process of claim 2 in which the mixture is mixed until a degree of separation of at least $10^{-3}$ is achieved.

4. The process of claim 3 in which the diamine in vaporous form is diluted with an inert gas or with vapors of an inert solvent.

5. The process of claim 2 in which the mixture leaving the mixing device is conveyed continuously through a cylindrical reaction chamber maintained at a temperature of 200° to 600° C. in a manner such that the flow has a Reynolds number of more than 4000 or a Bodenstein number of more than 100.

6. The process of claim 5 in which the mixture is present in the cylindrical reaction chamber until the reaction is completed.

7. The process of claim 5 in which the mixture leaving the reaction chamber in the form of a gas is cooled at a temperature such that the diisocyanate is condensed but any carbamic chloride of the diamine will be decomposed.

8. The process of claim 7 in which any uncondensed diisocyanate is separated from the gas mixture by washing the gas mixture with an inert solvent.

9. The process of claim 8 in which the inert solvent is recovered by distillation.

* * * * *